(12) United States Patent
Hannapel et al.

(10) Patent No.: US 8,936,026 B2
(45) Date of Patent: Jan. 20, 2015

(54) ORTHODONTIC APPLIANCE SHIELD

(75) Inventors: Eric D. Hannapel, Middleville, MI (US); David Gerard Jablonski, Alto, MI (US)

(73) Assignee: Orvance Technologies, LLC, Alto, MI (US)

(*) Notice: Subject to any disclaimer, the term of this patent is extended or adjusted under 35 U.S.C. 154(b) by 70 days.

(21) Appl. No.: 13/367,056

(22) Filed: Feb. 6, 2012

(65) Prior Publication Data

US 2012/0199138 A1  Aug. 9, 2012

Related U.S. Application Data

(60) Provisional application No. 61/440,549, filed on Feb. 8, 2011.

(51) Int. Cl.
- *A61C 5/14* (2006.01)
- *A61C 7/12* (2006.01)
- *A63B 71/08* (2006.01)

(52) U.S. Cl.
CPC ........... *A63B 71/085* (2013.01); *A63B 2209/10* (2013.01); *A61C 7/125* (2013.01)
USPC .......................................... 128/859; 128/861

(58) Field of Classification Search
USPC ........... 128/859, 861; 433/22; 602/41, 46, 54, 602/55
See application file for complete search history.

(56) References Cited

U.S. PATENT DOCUMENTS

| | | | |
|---|---|---|---|
| 2,257,709 A * | 9/1941 | Anderson | 433/25 |
| 3,327,580 A * | 6/1967 | Herweg | 84/453 |
| 3,844,286 A * | 10/1974 | Cowen | 604/77 |
| 4,044,762 A | 8/1977 | Jacoba | |
| 4,180,912 A | 1/1980 | Kesling | |
| 4,355,975 A | 10/1982 | Fujita | |
| 4,503,116 A | 3/1985 | Lapidus | |
| 4,512,740 A | 4/1985 | Kurz | |
| 4,527,975 A | 7/1985 | Ghafari et al. | |
| 4,559,013 A | 12/1985 | Amstutz et al. | |
| 4,687,441 A | 8/1987 | Klepacki | |
| 4,712,999 A | 12/1987 | Rosenberg | |
| 4,848,365 A | 7/1989 | Guarlotti et al. | |
| 4,901,714 A | 2/1990 | Jensen | |
| 4,913,654 A | 4/1990 | Morgan et al. | |
| 5,037,296 A | 8/1991 | Karwoski | |
| 5,160,260 A | 11/1992 | Chang | |
| 5,462,067 A | 10/1995 | Shapiro | |
| 5,469,865 A | 11/1995 | Minneman | |
| 5,509,805 A | 4/1996 | Jagmin | |
| 5,533,524 A | 7/1996 | Minneman | |
| 5,536,169 A | 7/1996 | Yousefian | |

(Continued)

OTHER PUBLICATIONS

International Search Report and Written Opinion for the International Searching Authority for PCT/US2012/024048 dated Aug. 22, 2012.

*Primary Examiner* — Patricia Bianco
*Assistant Examiner* — Keri J Nelson
(74) *Attorney, Agent, or Firm* — Price Heneveld LLP

(57) ABSTRACT

A protective shield is removably mounted over an orthodontic appliance in a user's mouth and includes an outer resilient compressible material layer joined to an inner adhesive layer. The shield is flexible for easy installation over all exposed surfaces of the orthodontic appliance; but is removable after a period of use. The outer resilient material layer of the shield can be formed of closed cell foam or a gelatinous material.

12 Claims, 4 Drawing Sheets

(56) References Cited

U.S. PATENT DOCUMENTS

| | | |
|---|---|---|
| 5,662,471 A | 9/1997 | Fogerty |
| 5,692,523 A | 12/1997 | Croli et al. |
| 5,732,715 A | 3/1998 | Jacobs et al. |
| 5,766,005 A | 6/1998 | Casey |
| 5,816,255 A | 10/1998 | Fishman et al. |
| 5,891,453 A | 4/1999 | Sagel et al. |
| 5,931,164 A | 8/1999 | Kiely et al. |
| 5,938,435 A | 8/1999 | Raspino, Jr. |
| 5,938,436 A | 8/1999 | Shevel |
| 5,954,500 A | 9/1999 | Spriggs |
| 6,003,515 A | 12/1999 | Maness |
| 6,080,923 A * | 6/2000 | Austin .................. 84/383 R |
| 6,092,524 A | 7/2000 | Barnes, Sr. |
| 6,318,371 B1 | 11/2001 | Tyszkiewicz |
| 6,447,290 B1 | 9/2002 | Williams |
| 6,551,579 B2 | 4/2003 | Sagel et al. |
| 6,584,978 B1 | 7/2003 | Brett et al. |
| 6,730,316 B2 | 5/2004 | Chen |
| 6,830,590 B1 | 12/2004 | Palahnuk et al. |
| 6,964,569 B2 | 11/2005 | Nordmo et al. |
| 7,128,072 B2 | 10/2006 | Bancroft |
| 7,128,899 B2 | 10/2006 | Chen |
| 7,305,990 B2 | 12/2007 | Mathias |
| 7,328,706 B2 | 2/2008 | Bardach et al. |
| 7,404,403 B2 | 7/2008 | Farrell |
| 7,530,355 B2 | 5/2009 | Berghash |
| 7,571,727 B2 | 8/2009 | Croll |
| 7,775,214 B1 | 8/2010 | Lesniak et al. |
| 7,862,801 B2 | 1/2011 | Chen |
| 7,862,802 B2 | 1/2011 | Kim et al. |
| 7,980,249 B2 | 7/2011 | Landi et al. |
| 8,007,277 B2 | 8/2011 | Fischer et al. |
| 8,074,659 B2 | 12/2011 | Hanna |
| 2005/0042173 A1 | 2/2005 | Besse et al. |
| 2005/0089820 A1 | 4/2005 | Allred |
| 2008/0280245 A1 | 11/2008 | Bitsack |
| 2009/0175928 A1 | 7/2009 | Maier et al. |
| 2010/0024833 A1 | 2/2010 | Swann et al. |
| 2010/0129763 A1 | 5/2010 | Kuo |
| 2010/0186756 A1 | 7/2010 | Koizumi et al. |
| 2011/0011703 A1 | 1/2011 | Kageyama et al. |
| 2011/0209713 A1 | 9/2011 | Lee |
| 2011/0315151 A1 * | 12/2011 | Schabert .................. 128/859 |
| 2012/0107768 A1 | 5/2012 | DiEdwardo |

* cited by examiner

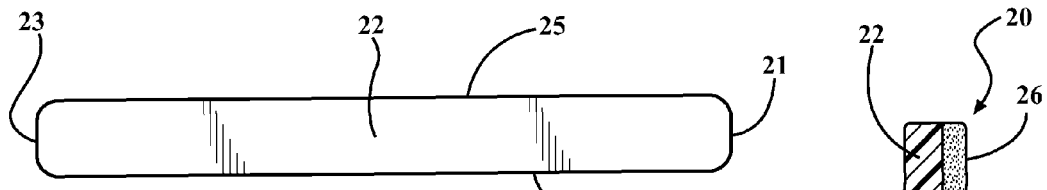
FIG. 2B
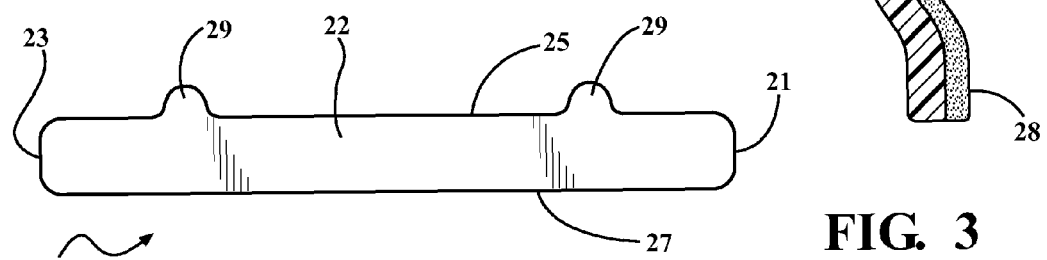
FIG. 2C
FIG. 3
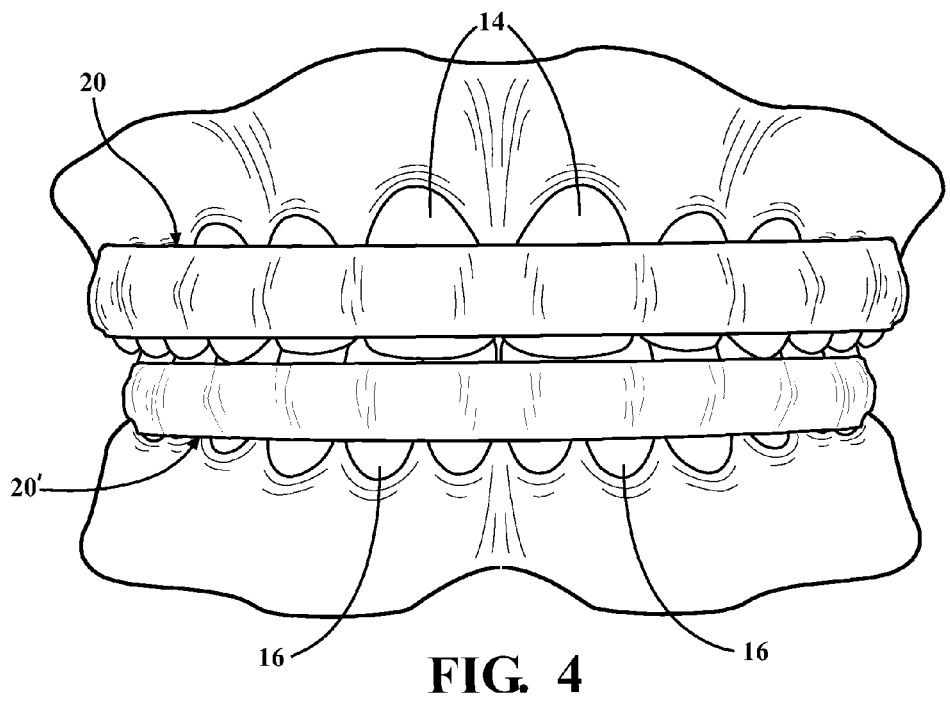
FIG. 4

ORTHODONTIC APPLIANCE SHIELD

CROSS REFERENCE TO CO-PENDING APPLICATION

The present application claims priority benefit to the Feb. 8, 2011 filing date of co-pending U.S. provisional patent application, Ser. No. 61/440,549 for an ORTHODONTIC APPLIANCE SHIELD filed in the names of Eric D. Hannapel and David G. Jablonski, the contents of which are incorporated herein in its entirety.

BACKGROUND

Sports which involve physical contact, such as football, hockey or lacrosse, commonly require helmets and mouth guards or teeth protectors. Athletes who wear orthodontic appliances, such as braces, face an extra hurdle in fitting the mouth guards around their orthodontic appliance.

Mouth guards and orthodontic appliance shields have been devised for protecting orthodontic appliances during such contact sports as well as protecting the inner surfaces of the athletes' lips and cheeks from injury. The use of such shields is becoming more important due to athletic event rules which require a person having a bleeding cut to be removed from the athletic contest until the bleeding stops.

Orthodontic appliance shields formed of pliable wax and plastic have been devised; but are cumbersome in fitting over the orthodontic appliance each time they are to be used. More rigid orthodontic appliance guards overcome this problem, but create additional problems relating to breathing difficulties and a higher cost.

Therefore, it would be desirable to provide an orthodontic appliance shield which addresses the above mentioned problems; while at the same time providing an easy to apply and easy to remove one time use.

SUMMARY

A protective shield applied over an orthodontic appliance on a user's teeth has a flexible strip having opposed longitudinal ends and opposed lateral side edges. The strip is in the form of an outer layer of a resilient compressible material joined to an inner adhesive layer. The inner adhesive layer provides adhesion of the resilient compressible material outer layer over all exposed surfaces of an orthodontic appliance while retaining the resilient outer layer on a user's teeth.

The adhesive layer can be applied over one entire surface of the outer layer. Alternatively, the adhesive layer can be applied in spaced longitudinal strips along the opposed side edges of the strips. The adhesive layer can be formed in discontinuous portions between the longitudinally opposed ends of the strip.

The outer layer of the strip can be formed of high density closed cell foam, such as polyolefin foam. The shield of the outer layer of the shield can also be formed of an elastomer, such as one of silicone, synthetic or natural rubber, and silicone gel.

In one aspect, the longitudinal side edges of the strip have a continuous linear shape. Alternately, one of the side edges can have two spaced enlarged areas or tabs projecting away from a major extent of the one side edge to cover a larger orthodontic appliance on a canine tooth.

BRIEF DESCRIPTION OF THE DRAWING

The various features, advantages and other uses of an orthodontic appliance shield will become more apparent by referring to the following detailed description and drawing in which:

FIG. 2B is a front elevational view of one aspect of an orthodontic appliance guard;

FIG. 2C is a front elevational view of another aspect of an orthodontic appliance guard;

FIG. 3 is a lateral cross sectional view of the orthodontic appliance guard shown in FIG. 2A;

FIG. 4 is a pictorial representation showing the installation of the orthodontic appliance guards on both upper and lower sets of teeth;

DETAILED DESCRIPTION

An orthodontic appliance shield or guard is disclosed in the form of a flexible guard or shield which is easily installed over an orthodontic appliance and which protects the surrounding inner soft lip and cheek tissue from contact with the sharp surfaces of the orthodontic appliance if the user's face is accidently struck, with force, such as during an athletic event. This minimizes the occurrence of cuts and bleeding in the lips and cheeks, which require the athlete to be removed from the athletic contest until the bleeding stops. The orthodontic appliance shield is easy to install and provides a one time, inexpensive, disposable use; while, at the same time, protecting the soft tissue in a user's mouth surrounding the orthodontic appliance from injury during physical contact in an athletic event.

Figure 1:
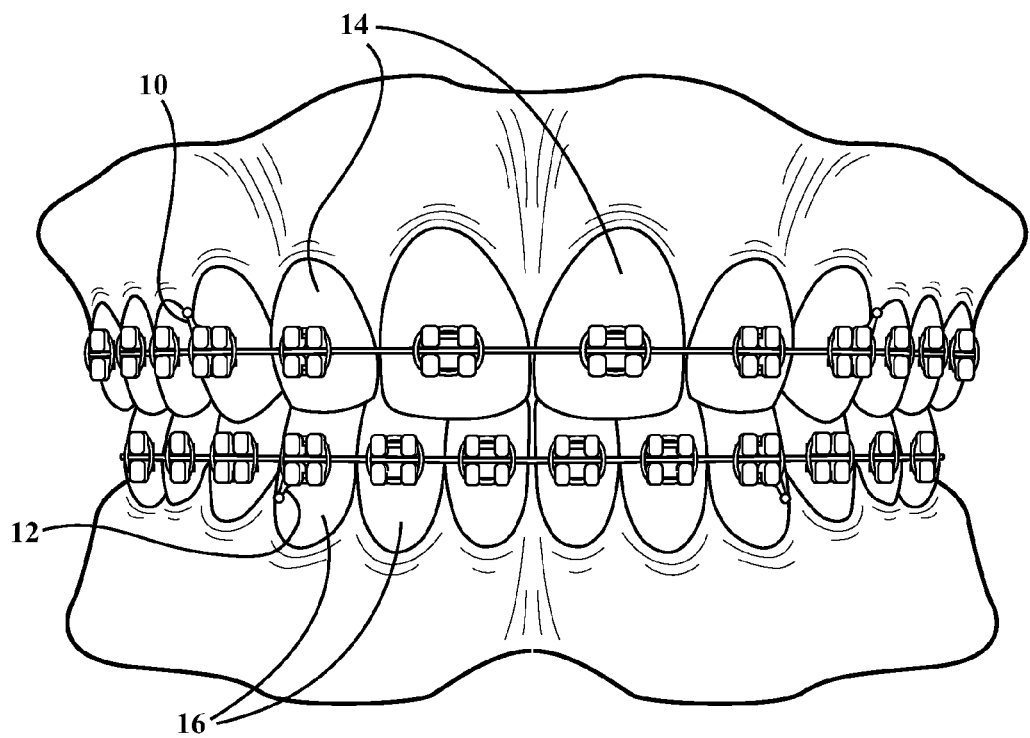
FIG. 1 is a pictorial representation of orthodontic appliances applied to upper and lower teeth.

Referring to FIG. 1, there is a depicted an example of orthodontic appliances 10 and 12 applied to a user's upper teeth 14 and lower teeth 16, respectively. It will be understood that the shape, attachment, length and number of teeth to which the orthodontic appliance 10 is applied is shown in FIG. 1 only by way of example as it will be understood that the orthodontic appliance 10 may take any necessary shape and configuration to suit a particular user's orthodontic requirements.

Figure 2A:
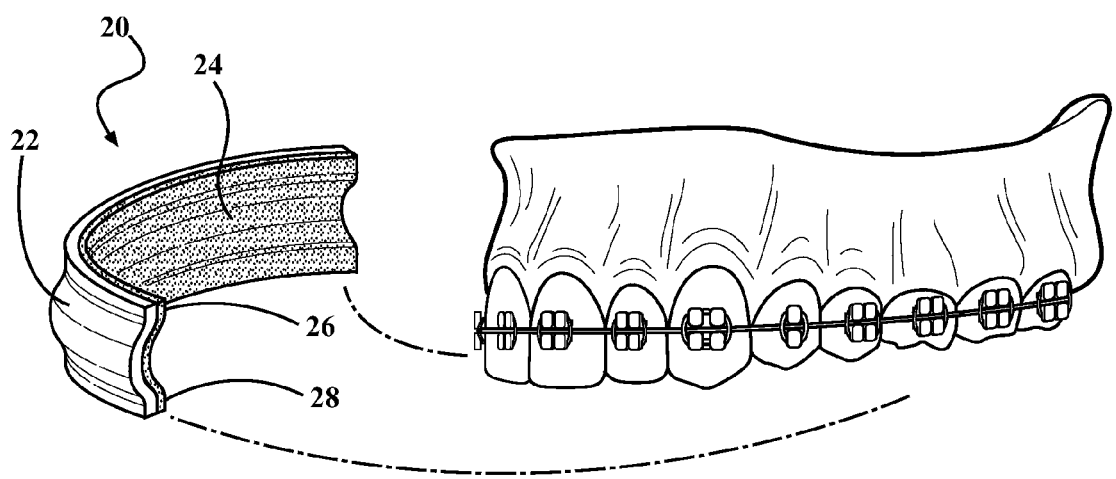
FIG. 2A is an exploded perspective view showing the application of an orthodontic appliance guard on a user's upper teeth.
Figure 5:
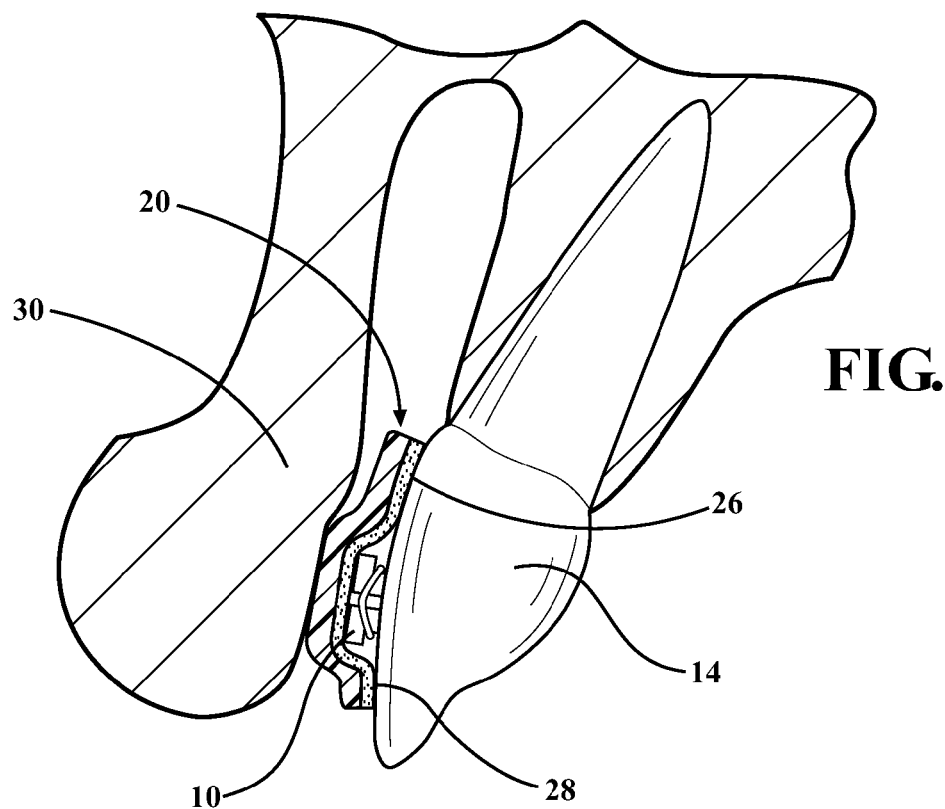
FIG. 5 is a lateral cross-sectional view shown in the installation of the orthodontic appliance guard of FIG. 2 on an upper tooth and appliance.

A shield or guard 20, shown in FIGS. 2A, 2B, 2C, 3, 4, and 5, is formed of an elongated strip of pliable, flexible material which is sized in width and length to cover the entire exterior surface of the orthodontic appliance 10 or 12. Although the shield 20 is shown in FIGS. 2A and 5 as being applied only over the appliance 10 on the upper teeth 14 of a user, a similar shield 20 may also be provided for the lower teeth 16 of the user as seen in FIG. 4.

The shield 20 may have a suitable thickness to facilitate flexibility and a comfortable feel to the user when applied over the user's orthodontic appliances. For example, the shield 20 can have a thickness of about 0.020 mm to about 1.5 mm. The thickness of the shield 20 could be from about 0.08 mm to about 0.80 mm.

Although the side edges of the shield 20 shown in FIG. 2B are generally linear, with rounded corners at the juncture with the longitudinal ends 21 and 23, the side edges 25 and 27 may have other shapes. For example, as shown in FIG. 2C, the shield 20 is formed with at least one or two elongated areas or tab 29 formed as a continuous part of one side edge 25. The elongated portions or tabs 29 provide an enlarged guard surface to cover the longer canine teeth of a user.

Figure 6:
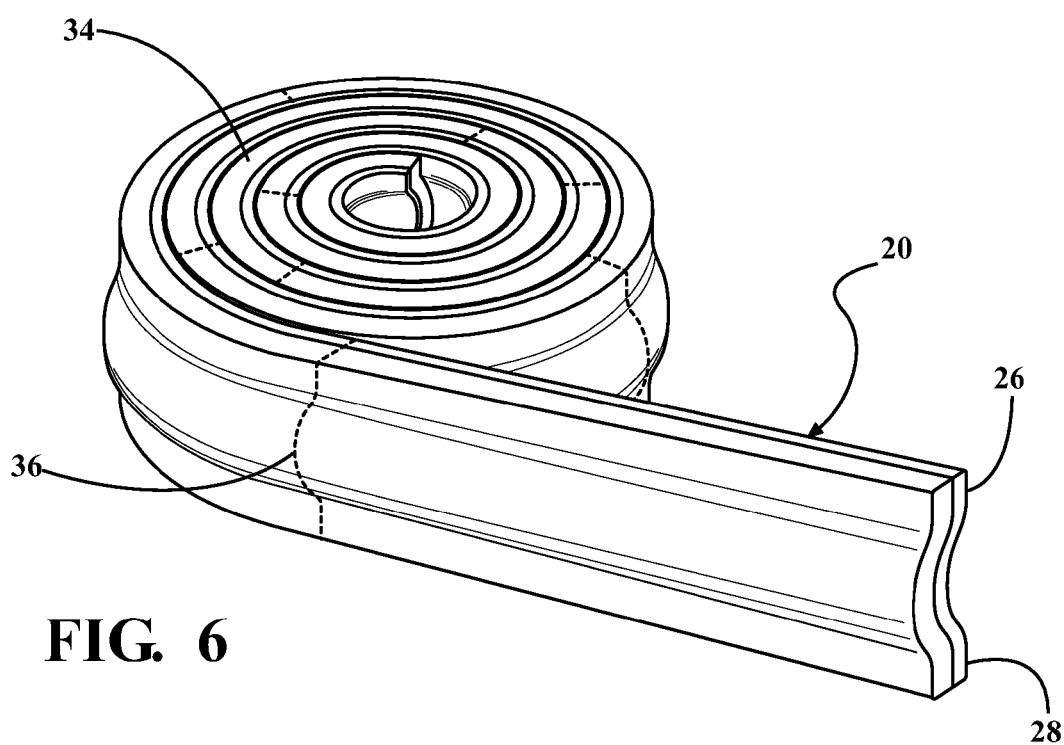
FIG. 6 is a pictorial representation of one aspect of a storage roll containing a plurality of orthodontic appliance guards shown in FIG. 2.

The shield 20 can be formed of a flexible, dental hygienic thermoplastic material. In one example, the shield 20 is formed of closed cell foam, such as a polyolefin. polyvinyl chloride, or urethane foam. These foams have shape memory and can be preformed into any shape, as shown in FIGS. 2 and 6.

In another example, the shield 20 is formed of a thin flexible polyolefin film or an elastomer, such as silicone, synthetic or natural rubber, urethane and the like. The elastomer can be filled with a gelatinous material, such as silicone gel.

The shield 20 has an outer layer 22 formed of the close cell foam or gelatinous material and a layer 24 of an adhesive material, such as a pressure sensitive adhesive or a hydrogel adhesive One adhesive composition which is suitable to form the adhesive layer 24 is polyvinylpryrrolidone (PVP) in the mixture with a humectant plasticizer such as polyethylene glycol and water. The mixture, which can be from about 20-80% by weight of PVP, to about 10% to about 50% by weight of the polyethylene glycol or other-humectant plasticizer, and about 5% to about 30% by weight of water, is thoroughly mixed and applied in a thin layer on one side of the flexible layer 22. The mixture is allowed to dry to facilitate easy handling and installation of the shield 20 over a user's orthodontic appliance 10. However, when the PVP is exposed to moisture in the user's mouth, it enters an active state to form an adhesive bond to the user's teeth to securely, but removably, retain the shield 10 on the user's teeth over the orthodontic appliance 10 for a period of time.

One specific example of an adhesive layer 24 is a mixture of about 50% PVP, about 40% polyethylene glycol and about 10% water, by weight.

It is also possible to form the adhesive layer 24 as a two part layer including the aforementioned mixture of PVP, humectant plasticizer and water and a substrate or base layer, such as a thin flexible polyolefin film. The polyolefin acts as a substrate to facilitate handling and drying of the mixture. The polyolefin can be adhesively joined to one surface of the flexible layer 22 of the shield 20 by pressure sensitive or tie adhesive.

Other tacky hydrophilic polymers are alkyl vinyl ether—maleic acid copolymer (commonly used as denture adhesive) and polyvinylpyrrolidone copolymers such as vinyl pyrrolidone-acrylic acid copolymer, vinyl pyrrolidone—vinyl acetate copolymer, and vinyl pyrrolidone-vinyl imidazole copolymer. Aqueous polymer solutions are made and cross-linked into solid hydrogels by radiation followed by drying for this application.

The humectant plasticizer added to those aqueous solutions are typically polyols like polyethylene glycol that retain water and prevent the hydrogel from becoming a hard and dry film. Other commonly used humectant plasticizers are glycerol, sorbitol, and propylene glycol.

The percent ranges by weight for these tacky hydrophilic polymers, humectants plasticizers, and water is the same as the PVP hydrogel example described above.

Figure 7:
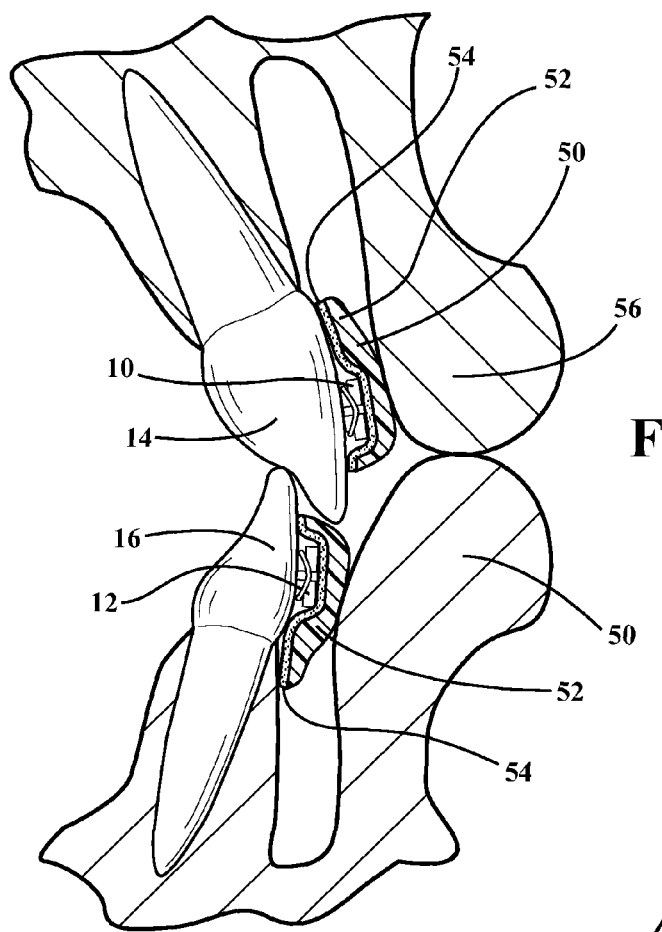
FIG. 7 is a lateral cross sectional view showing the mounting of another aspect of an orthodontic appliance guard shown on upper and lower teeth.

Although the entire surface of the shield 20 facing the teeth when in use, may be coated with the adhesive material 24 in a continuous layer, it is also possible to apply the adhesive layer 24 only to the flatter side end portions 26 and 28 of the shield 20 which contact the user's teeth 14 or 16 as shown in cross-section in FIGS. 7. In this aspect, the inner surface of the shield 20 which surrounds and contacts the appliance 10 or 12 is not adhesively fixed to the appliance 12.

It is also possible to coat the entire inner surface of the shield 20 with the adhesive layer 24 in continuous, longitudinally spaced strips along the length of the shield 20, or in discontinuous portions along the length and width of the shield 20.

The sticky adhesive material is selected to enable the shield 20 to be easily applied to the user's teeth 14 or 16 and wrapped around the appliance 10 or 12 while still being fixedly retained for a brief period of time, such as several hours, on the teeth to enable the user to participate in an athletic event. At the completion of the event, the user may simply grasp one edge of the shield 20 and pulls the shield 20 along its length to remove it from the user's teeth 14 or 16 and the orthodontic appliances 10 or 12 respectively mounted thereon.

In applying the strip 20, the user may bring one edge, such as the upper or lower end portions 26 or 28, into contact with the exposed portions of the user's teeth 14 or 16. The user then presses lightly on the side edge 26 or 28 of the shield 20 to firmly engage the adhesive layer 24 with the teeth 14 or 16. The user then smoothly conforms the shield 20 over the appliance 10 or 12 before bringing the opposed side edge 28 into contact with the teeth 14 or 16. The user again applies firm pressure to the side edge 28 to fixedly engage the adhesive layer 24 with the user's teeth 14 or 16.

In the use position as shown in FIG. 5, the shield 20 completely covers all of the exterior surfaces of the orthodontic appliances 10 or 12, and prevents the engagement of the sharp edges and portions of the orthodontic appliances 10 or 12 with the inner surfaces of the soft tissue of the user's lips or cheeks denoted generally by reference number 30 in FIG. 5. This prevents the orthodontic appliance 10 or 12 from causing injury to and bleeding from the lip or cheek tissue 30 when an external force, as frequently occurs during a contact or even a non-contact athletic event, from bringing the soft tissue 30 into forced engagement with the sharp edges, corners, or other portions of the orthodontic appliances 10 or 12.

The shield 20 thus minimizes injury to the soft tissue 30, which can prevent bleeding during an athletic event that previously would have required the athlete to remove himself or herself from the event until the bleeding stopped.

The shield 20 can be provided in a flat shape which is still conformable due to its inherent flexibility, into the installed shape shown in FIG. 5 where the end portions 26 and 28 are fixedly attached to the user's teeth 14 and an intermediate portion of the shield 20 extends away from the teeth and completely surrounds the external surfaces of the orthodontic appliance 10 or 12.

As shown in FIGS. 2, 3 and 6, the shield 20 may have a preformed arch-like shape more suitable to fit around a conventional orthodontic appliance 10 and 12. Even with the preformed shaped shown in FIGS. 2, 3, and 6, the shield 20 still has a sufficient degree of resiliency to enable the user to conform the shield 20 to the specific shape of the user's orthodontic appliances 10 or 12.

The shield 20 may be manufactured and packaged in a variety of forms. In one aspect, the shield 20 can be provided as a group of pre-sized, separate shields 20, each having the same predetermined length. The adhesive layer 24 may be covered by a peel-off non-adhering sheet, such as wax paper, which enables a single strip 20 to be separated from the remaining stack of strips 20 in a package.

Alternately, as shown in FIG. 6, the strips 20 can be formed in a continuous elongated strip wound in a roll 34. The end most strips 20 can be unrolled from the roll 34 and separated from the roll 34 by severing the strip 20 from the remaining roll 34 by means of a series of perforations or cuts 36 preformed at predetermined length intervals along the entire length of the continuous roll 34.

The strips 20 can also be formed in a continuous elongated strip while in a roll, such as roll 34, but without perforations or cuts preformed at predetermined length intervals. In this aspect, the user cuts a predetermined length from the strip 20 to suit the user's particular sized orthodontic appliance.

Figure 8:
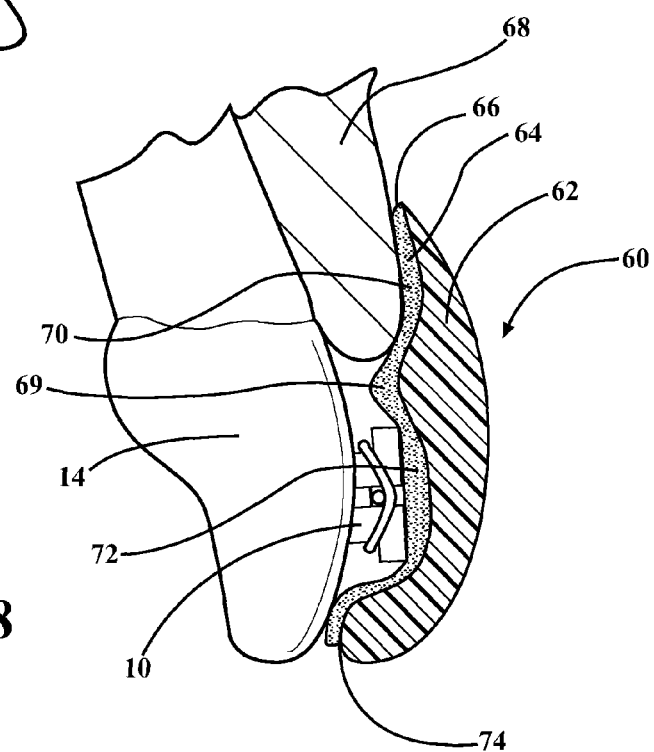
FIG. 8 is a lateral cross sectional view showing the mounting of another aspect of an orthodontic appliance shield covering a user's orthodontic appliance and a portion of the user's adjacent gum tissue.

Another aspect of the orthodontic appliance shield 50 is shown in FIGS. 7 and 8. It will be understood that although FIGS. 7 and 8 show the construction of the shield with a gelatinous material layer, the shield 50 could also be formed using the foam material described above.

The shield 50 is formed with an outermost gelatinous material layer 52 and an innermost adhesive layer 54, both of which may be constructed of the materials described above. In the aspect of the shield 50 shown in FIG. 7, the shield 50 has an elongated shape extending between opposed ends, both of which are positioned for releasable attachment to the user's teeth, representatively shown by tooth 14 in FIG. 7. The gelatinous layer 52, in this aspect, has a smooth outer shape, but areas with different width cross sections to accommodate positioning on the upper or lower teeth 14 and 16 of a user.

As shown in FIG. 7, the outer gelatinous layer 52 of the shield 50 on each of the upper and lower teeth 14 and 16 is positioned to contact the inner surface of the adjacent cheek or soft tissue 56 of the user's mouth to prevent contact between the tissue 56 and the sharp edges of the orthodontic appliance 10 or 12.

In the aspect of the shield 60 shown in FIG. 8, the shield 50 has an elongated width for both the gelatinous layer 62 and the adhesive layer 64. The elongated width enables the shield 60 to extend from a first end 66 located at a position removably adhesively affixed to the user's gum 68 adjacent to the user's tooth 14. The adhesive layer 64 and the inner surface of the gelatinous layer 62 transitions through a smoothly curved in and out sinuous shape from the one end 66 to an opposed end 74. This smoothly curved shape enables the shield 60 to completely cover the exposed surface of the orthodontic appliance 10 to prevent contact between the orthodontic appliance 10 and the surround soft tissue 56 of the user's mouth. As shown in FIG. 8, the inner adhesive layer 64 and the adjacent portion of the gelatinous layer 62 may curve inward at an intermediate portion 69 to curve over one side edge of the orthodontic appliance 10. The two adjacent curved portions or lobes 70 and 72 formed on the inner surface of the shield 60 enable the shield 62 smoothly extend from the end 74 removably adhesively fixed to the user's tooth 14 to the opposite end 66 which is removably, adhesively fixed to the gum 68 adjacent to the tooth 14.

What is claimed is:

1. An orthodontic appliance shield adapted to be applied to a user's teeth comprising:

a flexible generally planar strip having opposed longitudinal ends and opposed lateral side edges, the width of the strip adapted to cover the exterior outer surface of the teeth;

a longitudinally extending recess found in the strip between the opposed lateral side edges adapted to fit over an orthodontic appliance on a user's teeth;

the strip formed of an outer layer of a resilient compressible material and an inner adhesive layer; and the inner adhesive layer providing adhesion of the resilient compressible material outer layer over all exposed surfaces of the orthodontic appliance to retain the resilient outer layer on the user's teeth, wherein one of the lateral side edges of the strip includes at least one enlarged portion extending from a main extent of the one side edge of the strip.

2. The shield of claim 1 wherein: the adhesive layer is applied over one entire surface of the outer layer.

3. The shield of claim 1 wherein: the adhesive layer is applied in spaced longitudinal strips along the opposed lateral side edges of the strips.

4. The shield of claim 1 wherein: the adhesive layer is formed in discontinuous portions between the longitudinally opposed ends of the strip.

5. The shield of claim 1 wherein: the outer layer is formed of a high density closed cell foam.

6. The shield of claim 5 wherein: the foam is of polyolefin foam.

7. The shield of claim 6 wherein: the polyolefin foam is one of a polypropylene foam and a polyethylene foam.

8. The shield of claim 1 wherein: the outer layer of the strip is formed of an elastomer.

9. The shield of claim 8 wherein: the outer layer of the strip is formed of one of silicone, synthetic or natural rubber, and silicone gel.

10. The shield of claim 1 wherein: the opposed lateral side edges of the strip are substantially linear.

11. The shield of claim 1 wherein the inner adhesive layer reacts with moisture in the user's mouth to create adhesion.

12. An orthodontic appliance shield adapted to be applied to a user's teeth comprising:

a flexible generally planar strip having opposed longitudinal ends and opposed lateral side edges, the width of the strip adapted to cover the exterior outer surface of the teeth;

a longitudinally extending recess found in the strip between the opposed lateral side edges adapted to fit over an orthodontic appliance on a user's teeth;

the strip formed of an outer layer of a resilient compressible material and an inner adhesive layer; and the inner adhesive layer providing adhesion of the resilient compressible material outer layer over all exposed surfaces of the orthodontic appliance to retain the resilient outer layer on the user's teeth, wherein one of the lateral side edges of the strip includes longitudinally spaced enlarged portions extending from a main extent of the one side edge of the strip.

* * * * *

UNITED STATES PATENT AND TRADEMARK OFFICE
CERTIFICATE OF CORRECTION

| | | |
|---|---|---|
| PATENT NO. | : 8,936,026 B2 | Page 1 of 1 |
| APPLICATION NO. | : 13/367056 | |
| DATED | : January 20, 2015 | |
| INVENTOR(S) | : Hannapel et al. | |

It is certified that error appears in the above-identified patent and that said Letters Patent is hereby corrected as shown below:

In the Specification,

Column 1, line 62, "DRAWING" should be --DRAWINGS--;

Column 1, line 66, "drawing" should be --drawings--;

Column 2, line 10, "cross sectional" should be --cross-sectional--;

Column 2, line 21, "cross sectional" should be --cross-sectional--;

Column 2, line 24, "cross sectional" should be --cross-sectional--;

Column 2, line 45, before "depicted" delete "a";

Column 3, line 6, "tab" should be --tabs--;

Column 3, line 19, "close" should be --closed--;

Column 3, line 22, after "adhesive" insert --.--;

Column 3, line 63, after "humectants" insert --,--;

Column 4, line 3, "FIGS." should be --FIG.--;

Column 4, line 18, "pulls" should be --pull--;

Column 5, line 45, "surround" should be --surrounding--;

Column 5, line 51, after "62" insert --to--;

Column 5, line 53, after "removably" insert --,--;

In the Claims,

Column 6, claim 1, line 13, "," should be --;--;

Column 6, claim 11, line 37, after "wherein" insert --:--; and

Column 6, claim 12, line 54, "," should be --;--.

Signed and Sealed this
Twenty-second Day of September, 2015

Michelle K. Lee
*Director of the United States Patent and Trademark Office*